United States Patent
Fortkort

(10) Patent No.: US 11,577,034 B2
(45) Date of Patent: Feb. 14, 2023

(54) DISCRETE APPARATUS FOR SELF-ADMINISTRATION OF CANNABINOIDS

(71) Applicant: Daisy Elizabeth Fortkort, Austin, TX (US)

(72) Inventor: Daisy Elizabeth Fortkort, Austin, TX (US)

(*) Notice: Subject to any disclaimer, the term of this patent is extended or adjusted under 35 U.S.C. 154(b) by 524 days.

(21) Appl. No.: 16/055,020

(22) Filed: Aug. 3, 2018

(65) Prior Publication Data

US 2019/0183179 A1    Jun. 20, 2019

Related U.S. Application Data

(60) Provisional application No. 62/540,580, filed on Aug. 3, 2017.

(51) Int. Cl.
*A24F 40/40* (2020.01)
*A61M 15/06* (2006.01)
(Continued)

(52) U.S. Cl.
CPC ........... *A61M 15/06* (2013.01); *A24B 15/167* (2016.11); *A24F 40/40* (2020.01); *A24F 40/46* (2020.01); *A24F 40/485* (2020.01); *A61M 15/0001* (2014.02); *A24D 3/17* (2020.01); *A24F 40/20* (2020.01); *A61K 31/352* (2013.01); *A61M 2205/3653* (2013.01); *A61M 2205/8206* (2013.01)

(58) Field of Classification Search
None
See application file for complete search history.

(56) References Cited

U.S. PATENT DOCUMENTS

| D695,450 S | 12/2013 | Benassayag et al. |
| 9,333,229 B2 | 5/2016 | Bjorncrantz |

(Continued)

OTHER PUBLICATIONS

"Buy Vaporizers—Shop Best Weed Vapes for Sale." Grasscity United States Accessed Jun. 17, 2017. https://www.grasscity.com/vaporizers.

(Continued)

*Primary Examiner* — Kelly M Gambetta
*Assistant Examiner* — Katherine A Will
(74) *Attorney, Agent, or Firm* — John A. Fortkort; Fortkort & Houston PC

(57) ABSTRACT

A device is provided for the self-administration of cannabinoids. The device includes a container having an opening on a first end thereof, a cap which releasably engages said first end of said container, and an assembly, including first and second modules, which is removably placed inside of the container. The first module includes a first element equipped with first and second threading, a receptacle for said solid medium, said receptacle being equipped with at least one surface feature which slidingly engages said first threading, and a solid medium which is seated in said receptacle and which contains at least one cannabinoid. The second module is equipped with a filter and has a first threading disposed on a first terminal portion thereof. Various accessories may be releasably attached to the container or assembly. Methods of using the device are also described.

20 Claims, 11 Drawing Sheets

(51) Int. Cl.
| | |
|---|---|
| *A61M 15/00* | (2006.01) |
| *A24B 15/167* | (2020.01) |
| *A24F 40/46* | (2020.01) |
| *A24F 40/485* | (2020.01) |
| *A61K 31/352* | (2006.01) |
| *A24F 40/20* | (2020.01) |
| *A24D 3/17* | (2020.01) |

(56) References Cited

U.S. PATENT DOCUMENTS

| | | | | |
|---|---|---|---|---|
| D770,679 S | * | 11/2016 | Weigensberg | D27/189 |
| 9,498,002 B1 | | 11/2016 | Soreide | |
| 9,498,588 B2 | | 11/2016 | Benassayag et al. | |
| 9,730,472 B2 | | 8/2017 | Farrow | |
| D814,102 S | | 3/2018 | Lehoux | |
| 9,974,339 B2 | | 5/2018 | Heidl | |
| 10,039,325 B2 | | 8/2018 | Cameron et al. | |
| D832,498 S | | 10/2018 | Chen | |
| 10,111,468 B2 | | 10/2018 | Fornarelli | |
| 10,251,425 B2 | | 4/2019 | Schuler et al. | |
| 10,278,426 B2 | | 5/2019 | Gadas | |
| 10,327,479 B2 | | 6/2019 | Popplewell et al. | |
| D873,479 S | | 1/2020 | Lehoux | |
| 11,129,410 B2 | | 9/2021 | Barbaric et al. | |
| 2013/0152922 A1 | * | 6/2013 | Benassayag | A24D 3/17 128/202.21 |
| 2017/0119044 A1 | | 5/2017 | Oligschlaeger et al. | |
| 2017/0150756 A1 | | 6/2017 | Rexroad et al. | |
| 2017/0266397 A1 | | 9/2017 | Mayle et al. | |
| 2017/0295843 A1 | | 10/2017 | Storch | |
| 2018/0043115 A1 | * | 2/2018 | Gould | A24F 40/42 |
| 2018/0221605 A1 | | 8/2018 | Marks et al. | |
| 2018/0303165 A1 | | 10/2018 | Schuler et al. | |
| 2018/0317549 A1 | | 11/2018 | Sawalha | |
| 2019/0069600 A1 | | 3/2019 | Dang | |
| 2019/0087302 A1 | * | 3/2019 | Smith | A24F 47/008 |
| 2019/0364968 A1 | | 12/2019 | Fu et al. | |
| 2021/0360981 A1 | | 11/2021 | Memari et al. | |

OTHER PUBLICATIONS

"USA Assorted Color Dab Stick 7.'" Marijuana Packaging Accessed Jun. 17, 2017. https://marijuanapackaging.com/products/USA-assorted-color-dab-stick-7.

"USA 6.5' Assorted Color Honeycomb Mini Oil Rig 14mm" Marijuana Packaging Accessed Jun. 17, 2017. https://marijuanapackaging.com/products/6-5-assorted-color-honeycomb-mini-oil-rig-10mm.

"USA 12' Honeycomb w/ Hurricane Side Car Oil Rig Blue." Marijuana Packaging Accessed Jun. 17, 2017. https://marijuanapackaging.com/products/12-honeycomb-w-hurricane-side-car-oil-rig-blue-18mm.

"Junior Kit." Atmosrx. Accessed Jun. 17, 2017. https://www.atmosrx.com/product/junior-portable-wax-vape-pen.

"Brass Pipe De Luxe." Grasscity United States. Accessed Jun. 17, 2017. https://www.grasscity.com/brass-pipe-de-luxe.html.

"Bud Bomb Original Metal Hand Pipe: Chrome." Grasscity United States. Accessed Jun. 17, 2017. https://www.grasscity.com/the-bud-bomb-original-chrome.html.

"Cheech & Chong's the Ripper Ceramic Vaporizer Kit." Grasscity United States Accessed Jun. 17, 2017 https://www.grasscity.com/cheech-chong-s-the-ripper-ceramic-vaporizer-kit.html.

"Nectar Collector Dab Pipe: 6in Long—10mm Attachment—Clear." Marijuana Packaging Accessed Jun. 17, 2017. https://marijuanapackaging.com/products/6-nectar-collector-10mm.

"Eleaf Ismoka Istick 50W Box Mod Full Kit." Vapor Authority. Accessed Jun. 17, 2017. https://www.vaporauthority.com/products/genuine-eleaf-ismoka-istick-50w-box-mod-kit.

"Metal Pure Pipe: 8cm." Grasscity United States. Accessed Jun. 17, 2017. https://www.grasscity.com/metal-pure-pipe-8.html.

Kushmaster. "Nug Jug Marijuana Term." Stoner, May 13, 2016. https://stonerdays.com/nug-jug/.

"The Piece Pipe." Grasscity United States. Accessed Jun. 17, 2017. https://www.grasscity.com/the-piece-pipe.html.

"Pax 2." Pax Labs. Accessed Jun. 17, 2017. https://www.pax.com/products/pax-2?variant=13409044299891.

"Istick Pico Kit Firmware Upgradeable: EleafWorld." Eleaf electronic cigarette, Aug. 9, 2021. https://www.eleatworld.com/istick-pico-kit/.

Yocan Vaporizer. "Yocan—Best Wax Pen L Vape Pens L Portable Vape L Yocanvaporizer." Yocan Vaporizer. Accessed Jun. 17, 2017. https://www.yocanvaporizer.com/.

"Silverstick Filtered One-Hitter // Weedgadgets." WEEDGADGETS, Apr. 25, 2021. https://www.weedgadgets.com/silverstick-filtered-one-hitter-pipe/.

"Spark Plug Stealth Pipe." Grasscity United States. Accessed Jun. 17, 2017. https://www.grasscity.com/spark-plug-stealth-pipe.html.

"Stealthy Keychain Pipe // Weedgadgets." WEEDGADGETS, Dec. 8, 2019. https://www.weedgadgets.com/stealthy-keychain-pipe/.

"King Amazed—Metal Smoking Pipe by Red-Eye." Grasscity United States. Accessed Jun. 17, 2017. https://www.grasscity.com/king-amazed-metal-pipe-by-red-eye.html.

* cited by examiner

DISCRETE APPARATUS FOR SELF-ADMINISTRATION OF CANNABINOIDS

CROSS-REFERENCE TO RELATED APPLICATIONS

This application claims the benefit of priority from U.S. Provisional Application No. 62/540,580, filed Aug. 3, 2017, having the same inventors, and the same title, and which is incorporated herein by reference in its entirety.

FIELD OF THE DISCLOSURE

The present disclosure relates generally to consumer products designed for the use of cannabis and related products, and more particularly to devices and methodologies for the discrete use of such products.

BACKGROUND OF THE DISCLOSURE

Cannabinoids are a class of chemical compounds that are biochemically active with respect to cannabinoid receptors in the human brain. This class of compounds include the phytocannabinoid tetrahydrocannabinol (THC), which is the primary psychoactive compound found in cannabis.

The recreational and medical use of cannabinoids has become common in many countries. In such uses, cannabinoids are frequently provided as sticky oils or waxes known as "concentrates". Such concentrates (which are also referred to as wax dabs, budder, honey oil, 710, and by various other names) contain concentrated doses of cannabis that are made by extracting THC and other cannabinoids, typically by using a solvent such as butane or carbon dioxide.

Various devices have been developed in the prior art for vaporizing or smoking cannabis or concentrates. For example, various glass pipes have been developed which may be utilized to smoke concentrates. These include the glass pipes sold under the trade name "The Honeycomb Oil Rig", which features a honeycomb percolator designed to limit the intake of tar during smoking.

Various so-called pen vaporizers have also been developed in the art. These include the pen vaporizers marketed under the tradename AtmosRx Jr Vaporizer™, which comprise a mouthpiece, a heating chamber, a battery, a USB charger and a packing tool. These also include the 650 mah wax dab pen vaporizers sold under the tradename Evolve™, which are equipped with a coil cap containing a quartz heating coil therein. The heating coil vaporizes the wax dab, while the coil cap prevents the melted wax from leaking out, and also keeps prevents the mouthpiece from becoming too hot.

Other notable vaporizers include the ceramic vaporizer sold under the tradename Cheech & Chong's The Ripper Ceramic Vaporizer Kit™, and sometimes referred to simply as The Ripper™. This vaporizer is designed for use with waxy oils and concentrates, and features a full-ceramic coil-less atomizer intended to provide even heat distribution. The Ripper™ has a single control LEI) button, a 950 mAh battery and a five-click lock feature for safety. The Ripper vaporizer purportedly heats up fast to provide 15 seconds of continuous use, and is said to generate thick clouds of vapor. The removable mouthpiece exposes the chamber that can be easily loaded with the provided dab tool, while the flat base provides stability. The compact device measures 11.5 cm (4.5 inches) in length, and comes packaged in a decorative box filled with an array of accessories. This concentrate vaporizer is rechargeable through the provided micro USB charger. The accessories include a ripper vaporizer, a 950 mAh battery, a ceramic atomizer, a micro USB charger, a dab tool with a silicone sleeve, and a user manual.

Other notable devices in the art include the herb pipe sold under the tradename Sparkplug™. The components of this pipe are detachable to obfuscate the fact that this piece is actually a pipe designed for smoking herbs. The pipe has a detachable lid on its bowl that can be unscrewed, thus allowing the user to preload the pipe and store it without any spillage until use. The metal body is said to ensure that the smoke cools down on its way to the user's lungs. For best results, the seller recommends that a metal screen be placed in the bowl of the pipe to prevent the inhalation of ash and herb crumbs.

Other metal pipes known to the art include the anodized aluminum smoking pipes sold under the brand name A'maze'd™. These smoking pipes include a 'maze' filtration system, which purportedly works by directing smoke through a 32 cm long convoluted path to cool it down.

Still other metal pipes known to the art include those sold under the tradename "Bud Bomb". These devices are equipped with an internal helical chamber through which smoke travels as it is inhaled by the user, thus cooling it down. The device may be disassembled into its four component pieces (the mouthpiece, helix, main cover and the bowl chamber) for cleaning. Accumulated tar within the device can purportedly be cleaned off by heating the device over a flame.

Other metal pipes known to the art include the three-piece metal smoking pipes sold under the tradename The Piecepipe™. This device, which is also designed to function as a keychain, is a precision made, three-piece smoking device. For cleaning, the pipe has a cylinder that can be divided into two halves. The stash chamber is designed to hold extra tobacco or a herbs. This device is equipped with air pockets that keep the mouthpiece from getting hot. In operation, the user clicks and locks the device into position to enable its different modes. These include a stealth mode for odor-free storage; a smoking mode for smoking; and a stash mode for storing tobacco or herbs. The device may also be fully unclicked to enable a clean mode.

BRIEF DESCRIPTION OF THE DRAWINGS

FIG. 12 is a top view of the third module in the embodiment of FIGS. 2-4.

FIG. 13 is a bottom view of the third module in the embodiment of FIGS. 2-4.

FIG. 14 is a side view of the capsule in the embodiment of FIGS. 2-4.

FIG. 15 is a top view of the capsule in the embodiment of FIGS. 2-4.

FIG. 16 is a bottom view of the capsule in the embodiment of FIGS. 2-4.

FIG. 17 is a top view of the container in the embodiment of FIGS. 2-4.

FIG. 18 is a side view of the container in the embodiment of FIGS. 2-4.

FIG. 19 is a bottom view of the container in the embodiment of FIGS. 2-4.

FIG. 20 is a top view of the cap of the container in the embodiment of FIGS. 2-4.

FIG. 21 is a side view of the cap of the container in the embodiment of FIGS. 2-4.

FIG. 22 is a bottom view of the cap of the container in the embodiment of FIGS. 2-4.

FIG. 23 is an exploded perspective view of a third embodiment of a device in accordance with the teachings herein.

SUMMARY OF THE DISCLOSURE

Figure 1:
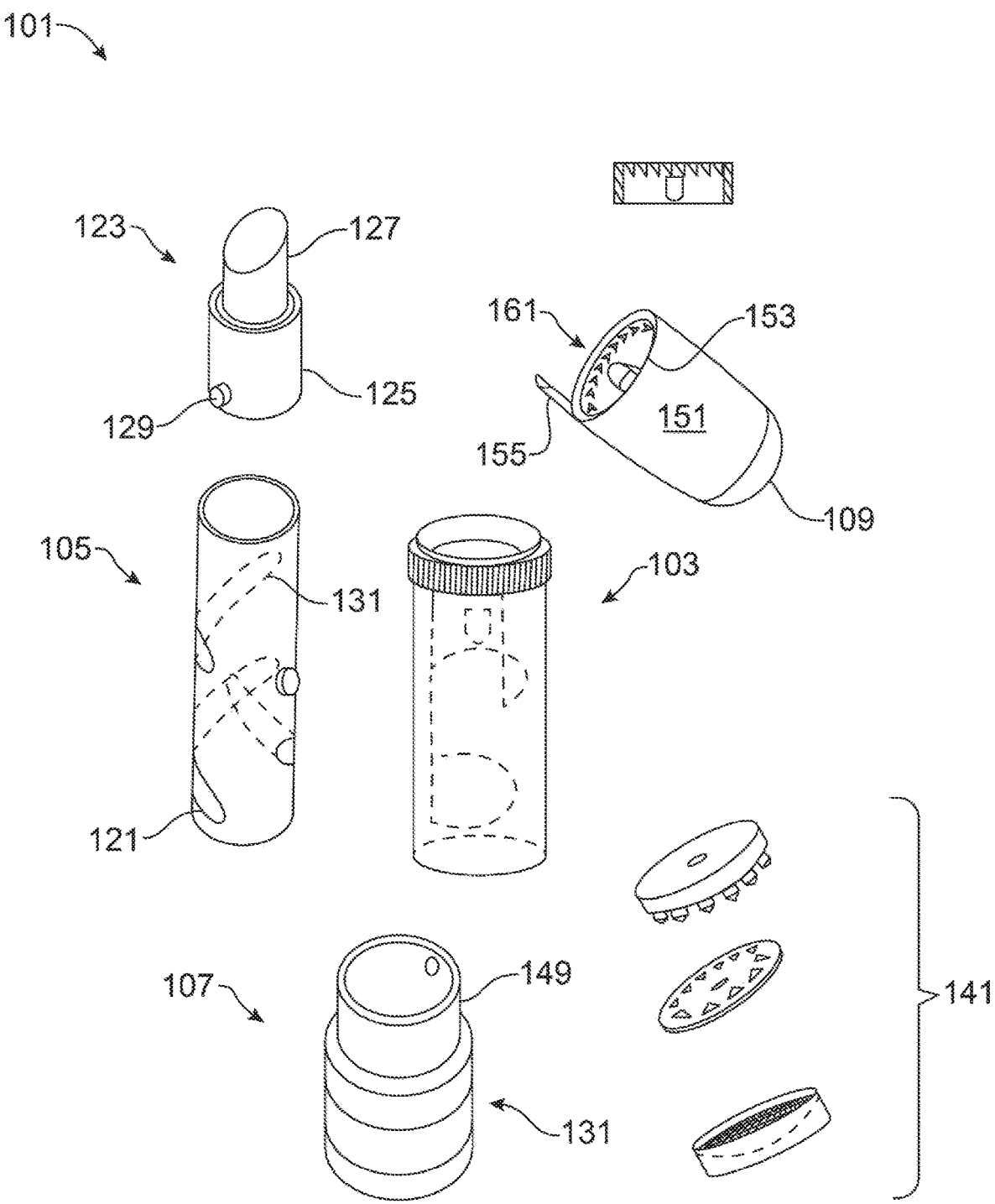
FIG. 1 is an exploded perspective view of a first embodiment of a device in accordance with the teachings herein.

In one aspect, a vaporizer is provided which comprises a first module which is equipped with a first set of threads and which has first and second opposing ends; a second module which is connected to the second end of said first module by way of a rotatable joint; a filter; a third module having an exterior body with a first plurality of apertures therein and equipped with (a) a resilient opening which releasably engages said second module, (b) a thermally conductive container which sits in said exterior body, and (c) a heating module which heats said exterior container on command; and a fluidic flow path which extends from said first plurality of apertures through said third module, said rotatable joint, said filter, said second module and said first and second opposing ends of said first module.

In another aspect, a device is provided for the self-administration of cannabinoids. The device comprises (a) a container having an opening on a first end thereof; (b) a cap which releasably engages said first end of said container; (c) a first module removably disposed within said container, said first module including (i) a first element equipped with first and second threading, (ii) a receptacle for said solid medium, said receptacle being equipped with at least one surface feature which slidingly engages said first threading, and (iii) a solid medium which is seated in said receptacle and which contains at least one cannabinoid; and (d) a second module which is equipped with a filter and which has a first threading disposed on a first terminal portion thereof.

In another aspect, a device is provided for the self-administration of cannabinoids. The device comprises (a) a container having an opening on a first end thereof; (b) a cap which releasably engages said first end of said container; and (c) an assembly which is disposed within said container and which comprises a first module which releasably engages a second module. The first module comprises (i) a housing element equipped with first and second threading, (ii) a receptacle which is disposed within said housing element and which is equipped with at least one surface feature which slidingly engages said first threading, and (iii) a solid medium which is seated in said receptacle and which contains at least one cannabinoid. The second module comprises (i) a first component which is equipped with a third threading, (ii) a second component which is equipped with a fourth threading and which is jointedly connected to said first component, and (iii) a filter.

In a further aspect, a device for the self-administration of cannabinoids. The device comprises (a) a container having first and second opposing ends with first and second openings therein, respectively; (b) a cap which releasably engages said first end of said container; (c) a first module releasably disposed within said container, said first module including (i) a first element equipped with first threading, (ii) a receptacle equipped with at least one surface feature which slidingly engages said first threading, and (iii) a solid medium which is seated in said receptacle and which contains at least one cannabinoid; and (d) a second module which is equipped with a filter and which releasably engages said second end of said container.

DETAILED DESCRIPTION

While the various devices noted above for smoking or vaporizing cannabis-based waxes or concentrates may have some desirable features, these devices also suffer from various infirmities. For example, some of these devices are immediately recognizable as drug paraphernalia. This is undesirable for users of these products who wish to remain discrete.

Many of these devices are also not childproof. Since vaporizers contain a concentrated form of tetrahydrocannabinol (THC), the possibility exists that a child encountering the device could ingest the concentrate.

Moreover, these devices are typically rigid, and are often somewhat linear. This not only limits the manner in which they can be used, but also places limits on the accessories that can be utilized with them. This is a key limitation, since the market for accessories for these devices is significant and somewhat untapped.

Finally, many of these devices are expensive and have designs that are not amenable to cleaning after use. Consequently, the user is required to perform time-consuming cleaning operations on them in order to maintain them in usable condition.

It has now been found that some or all of the foregoing infirmities may be overcome with the devices and methodologies described herein. In a preferred embodiment, these devices allow cannabis-based waxes or concentrates to be carried discretely on the person of the user. For example, in an especially preferred embodiment, the device, or the cannabis concentrate portion of it, is made to resemble a lipstick or chap stick applicator (or portion thereof). In addition to masking the purpose of the device, such applicators can be readily equipped with child-proof locks to prevent the accidental ingestion of the cannabis concentrate by a child.

Preferred embodiments of the devices disclosed herein are also equipped with a swivel, a ball socket, or another suitable rotating means that allows at least one component the body of the device to be rotated with respect to another one. The rotating means is preferably provided with an interior channel that allows a fluidic flow to pass through it. Consequently, the rotating means adds functionality and flexibility of use to the device without hindering its operation (that is, without hindering fluidic flow through the device).

Finally, preferred embodiments of the devices disclosed herein are modularized, and are equipped with inexpensive modules that serve to vaporize or ignite the concentrates that are utilized with. This allows these modules to be disposed and replaced when they become soiled, thus obviating the need for the user to clean them or replace the entire device.

FIG. 1 depicts a first particular, non-limiting embodiment of a device for the self-administration of cannabinoids in accordance with the teachings herein. The device 101 depicted therein includes a container 103 which has a first module 105 disposed therein, and which rotatingly engages a second module 107, and a cap 109.

The first module 105 comprises a housing 121 and a capsule 123. The capsule 123 extends from, and retracts into, the housing 121 by rotating in relation thereto. The capsule 123 comprises a base 125 having a payload 127 mounted thereon. The payload 127 may comprise, for example, a wax medium having THC disposed therein. The base 125 is equipped with a protrusion 129 on a surface thereof which slidingly engages a slot 131 defined in the wall (and preferably on the interior surface) of the housing 121.

The second module 107 is equipped with a grinder 141 and a storage compartment 143. The grinder 141 includes opposing rotatable elements 143, 145 and 147 which are equipped with opposing blades or protrusions, and which rotate with respect to each other to grind a material into a fine powder. The second module 107 may be releasably attached to the housing 121 or the container 103 by way of threading 149 or by other suitable means, or may be permanently attached thereto by way of, for example, a suitable adhesive.

The cap 109 comprises a body 151 having a circular opening 153 therein which slides over the exposed surface of the capsule 123. The cap 109 is equipped with a protrusion 155 which extends therefrom, and which may be used to cut the payload 127. The cap 109 is further equipped with suitable features 161 which operate in conjunction with features defined in the container 103 to impart a child-proof locking mechanism to the device 101.

FIGS. 2-10 depict a second particular, non-limiting embodiment of a device for the self-administration of cannabinoids in accordance with the teachings herein. The device 201 is similar in some respects to the device 101 of FIG. 1. Thus, the device 201 includes a container 203 which has a first module 205 disposed therein, and which rotatingly engages a second module 207 (see FIG. 3) and a cap (not shown).

The first module 205 comprises a housing 221 and a capsule 223 (shown in greater detail in FIGS. 14-16). The capsule 223 extends from, and retracts into, the housing 221 by rotating in relation thereto. The capsule 223 comprises a base 225 having a payload 227 mounted thereon. The payload 227 may comprise, for example, a wax medium having THC disposed therein. The base 225 is equipped with a protrusion 229 on a surface thereof which slidingly engages a slot 231 or track defined in the wall (and preferably on the interior surface) of the housing 221.

Figure 2:
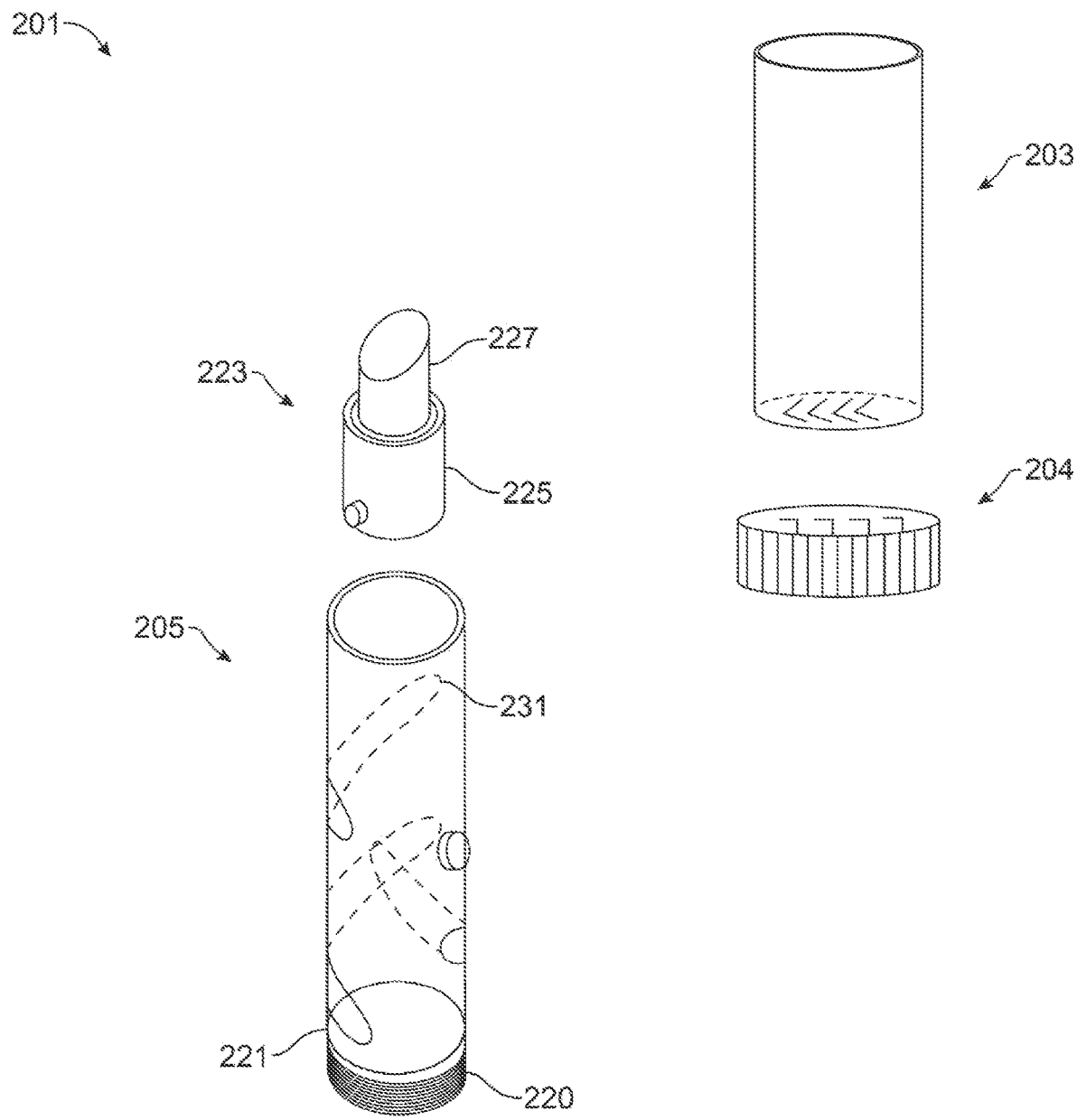
FIGS. 2-4 are an exploded perspective views of modules of a second embodiment of a device in accordance with the teachings herein.
Figure 3:
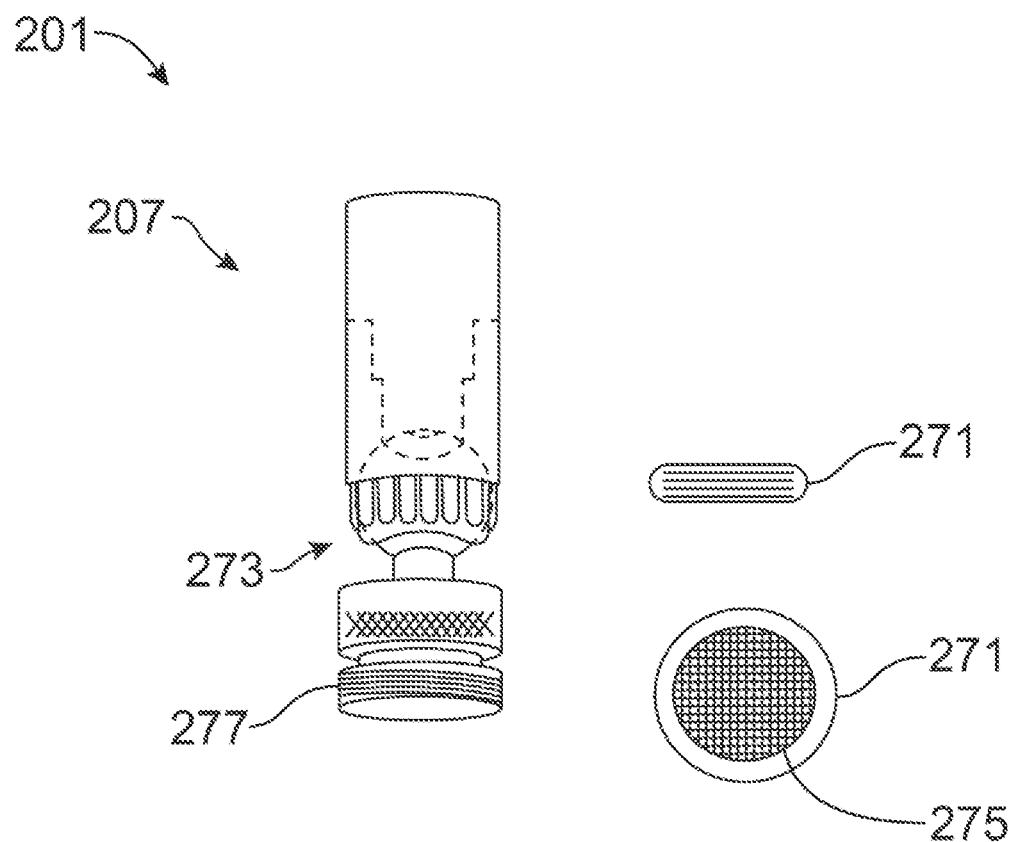

The embodiment 201 of FIG. 2 utilizes a container 203 (shown in greater detail in FIGS. 17-19) equipped with a locking cap 204 (shown in greater detail in FIGS. 20-22). The container 203 and cap 204 are preferably of the type commonly utilized in the pharmaceutical industry. Hence, in a preferred embodiment, the container 203 and cap 204 require the user to press down on the cap while rotating it in order to remove the cap 204 from the container 203. In variations of this embodiment, the container 203 and cap 204 may be equipped with indicia (which may include, for example, arrows or triangles) which must be properly aligned in order for the cap 204 to be removed from the container 203.

The first module 205 in this particular embodiment is equipped with male threading 220. The male threading 220 rotatingly engages a complimentary set of female threading 222 on the second module 207, thus allowing the first module 205 and the second module 207 to be releasably attached to each other.

Figure 5:
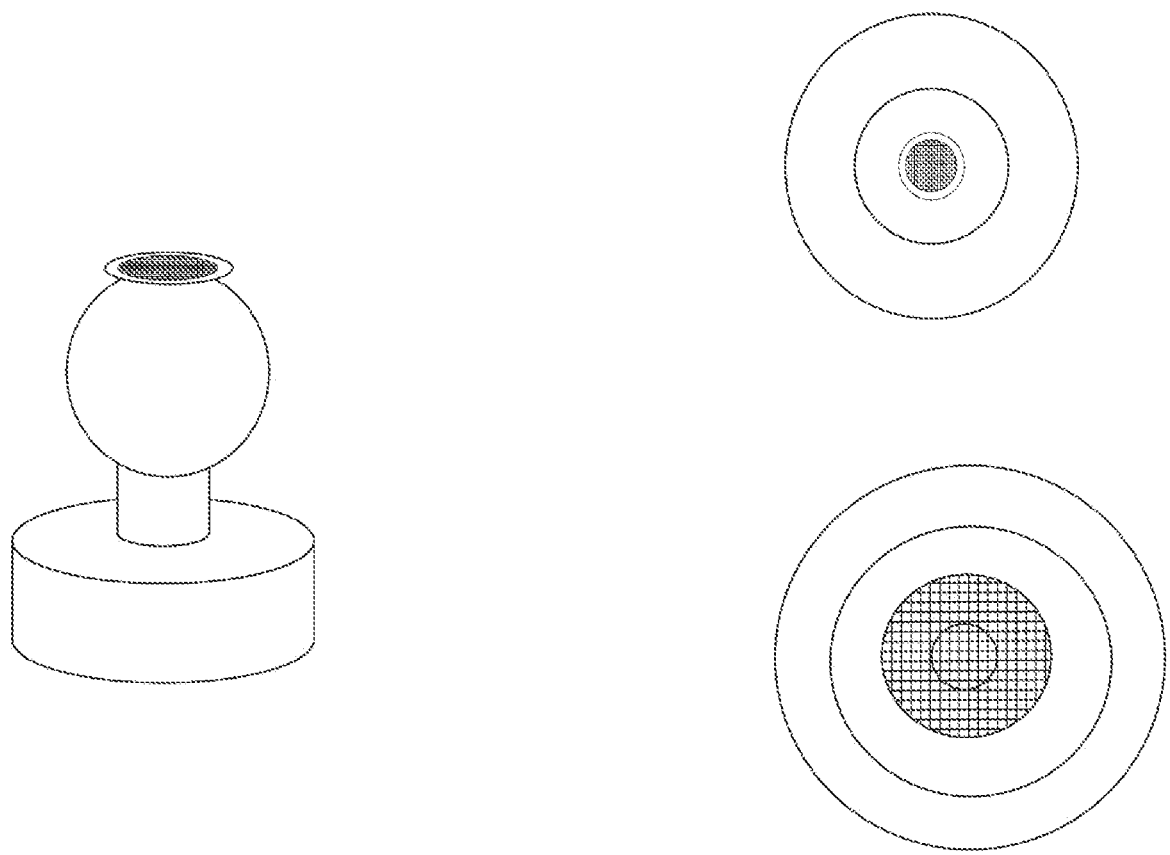
FIG. 5 is a top view of a rotatable joint in the embodiment of FIGS. 2-4.
Figure 6:
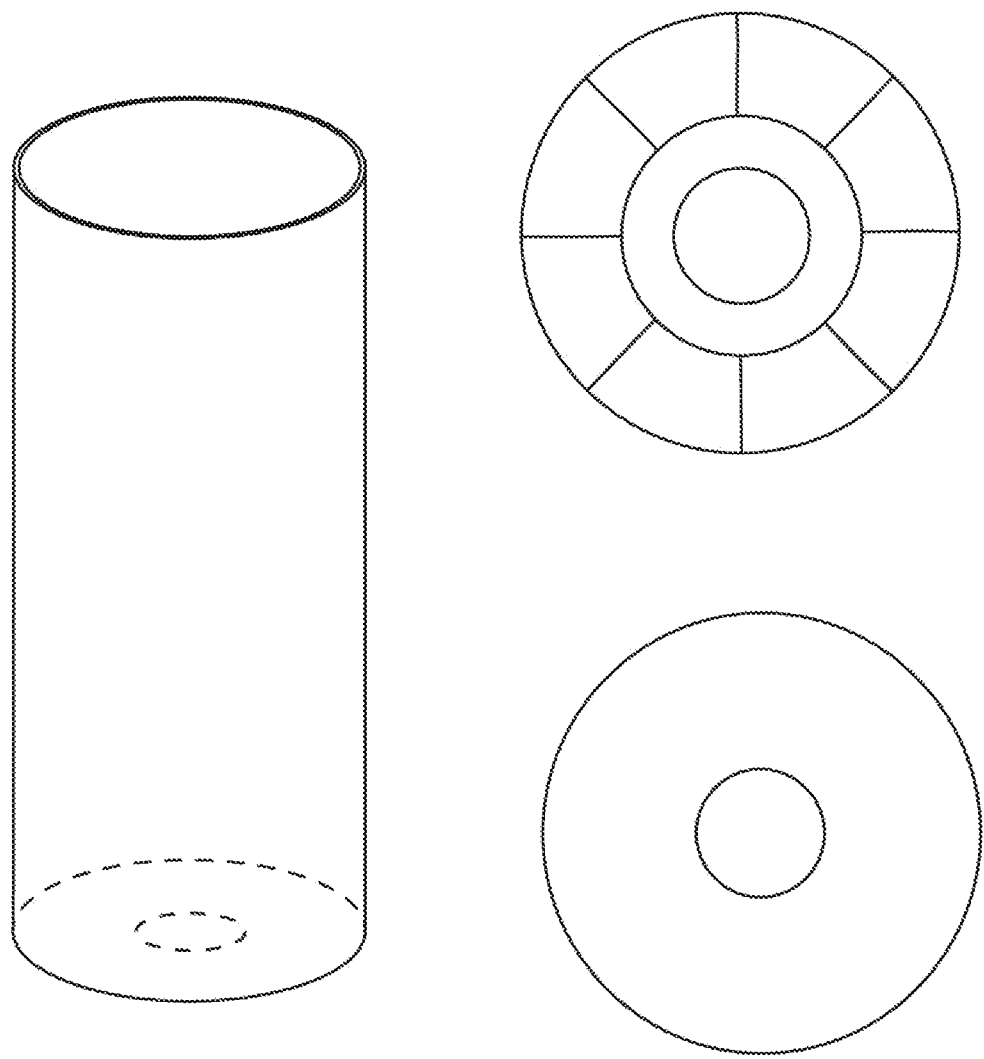
FIG. 6 is a side view of a rotatable joint in the embodiment of FIGS. 2-4.
Figure 7:
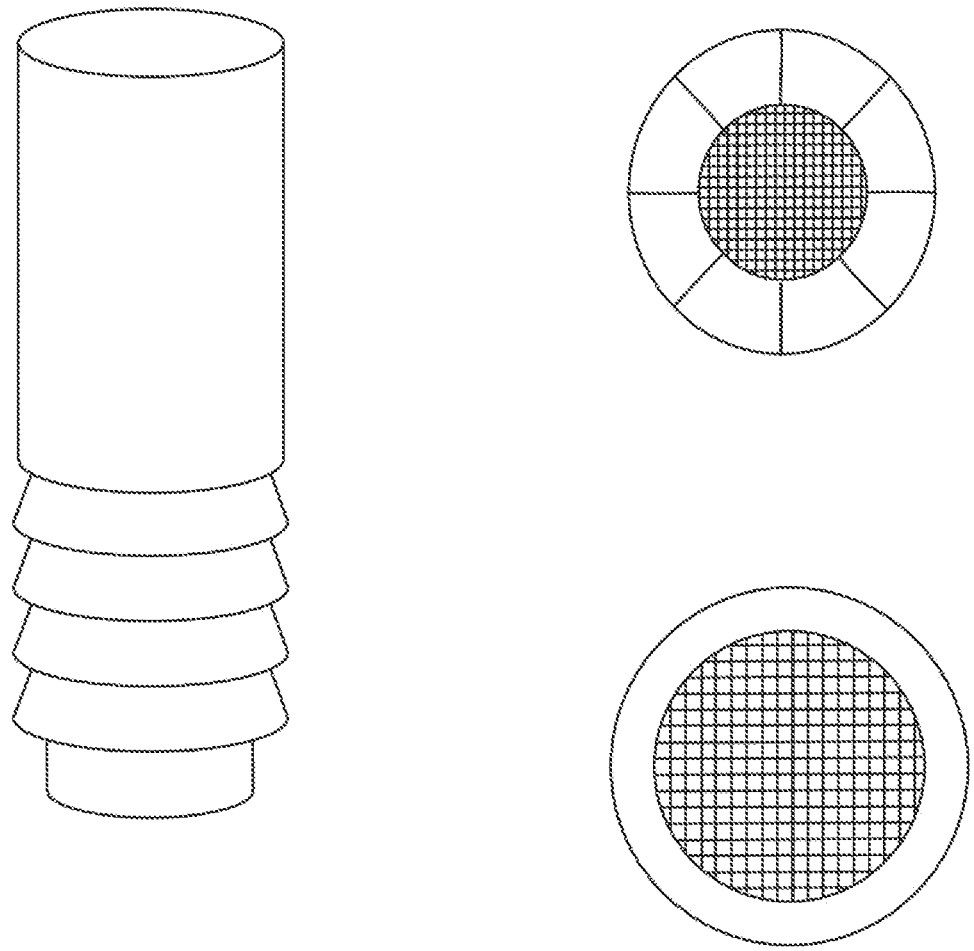
FIG. 7 is a bottom view of a rotatable joint in the embodiment of FIGS. 2-4.
Figure 8:
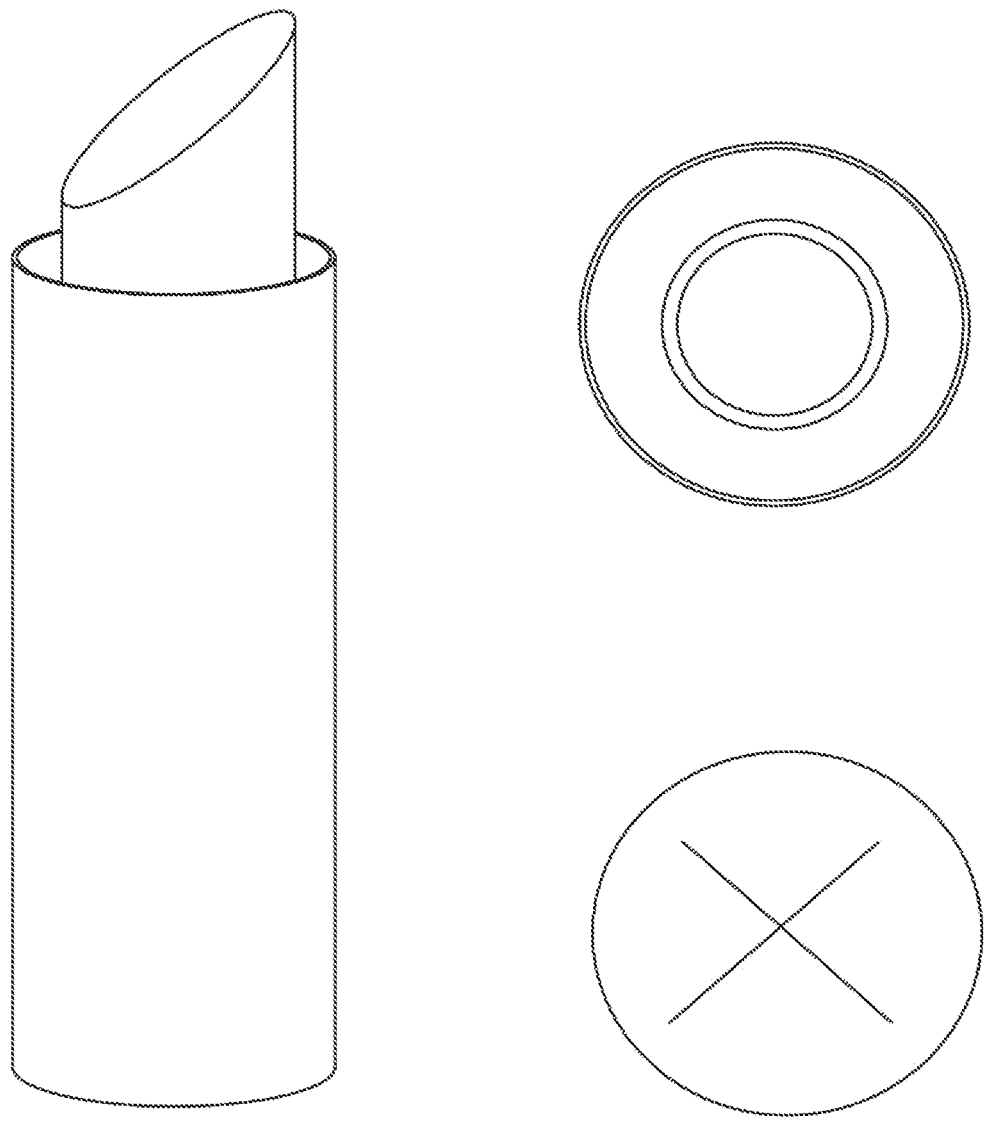
FIG. 8 is a top view of a chamber which encloses second module in the embodiment of FIGS. 2-4.
Figure 9:
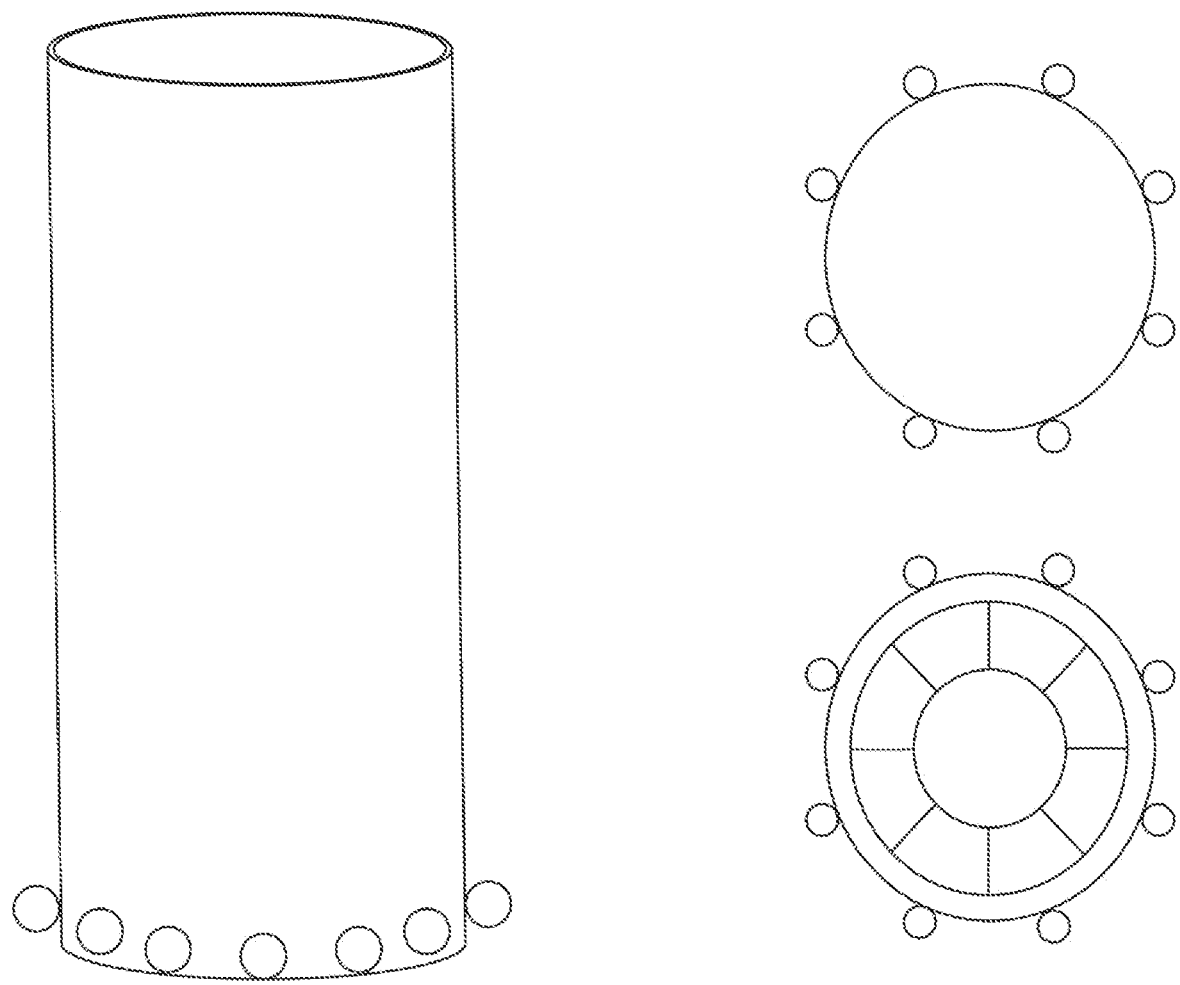
FIG. 9 is a perspective view of a chamber which encloses second module in the embodiment of FIGS. 2-4.
Figure 10:
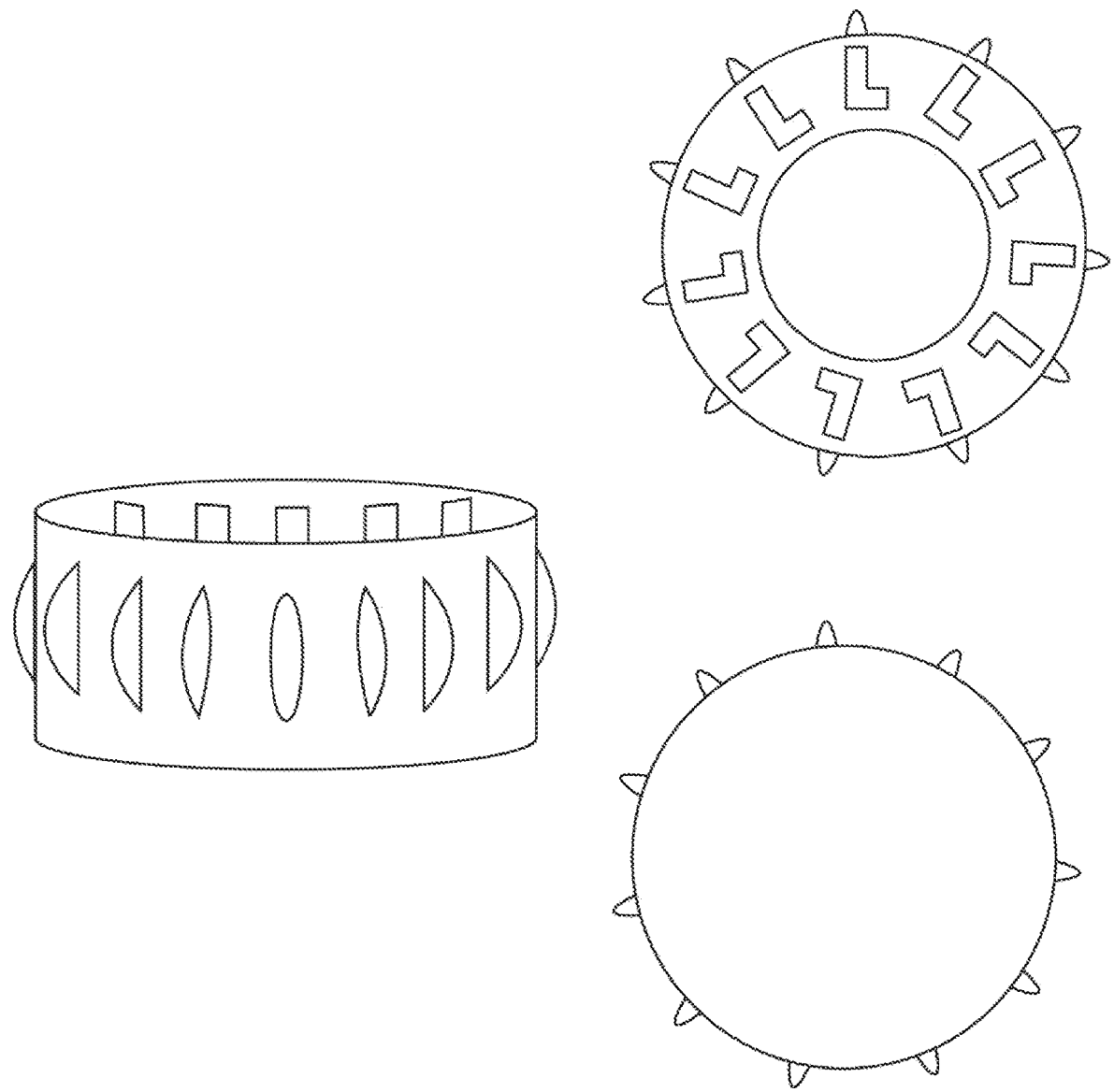
FIG. 10 is a bottom view of a chamber which encloses second module in the embodiment of FIGS. 2-4.
Figure 11:
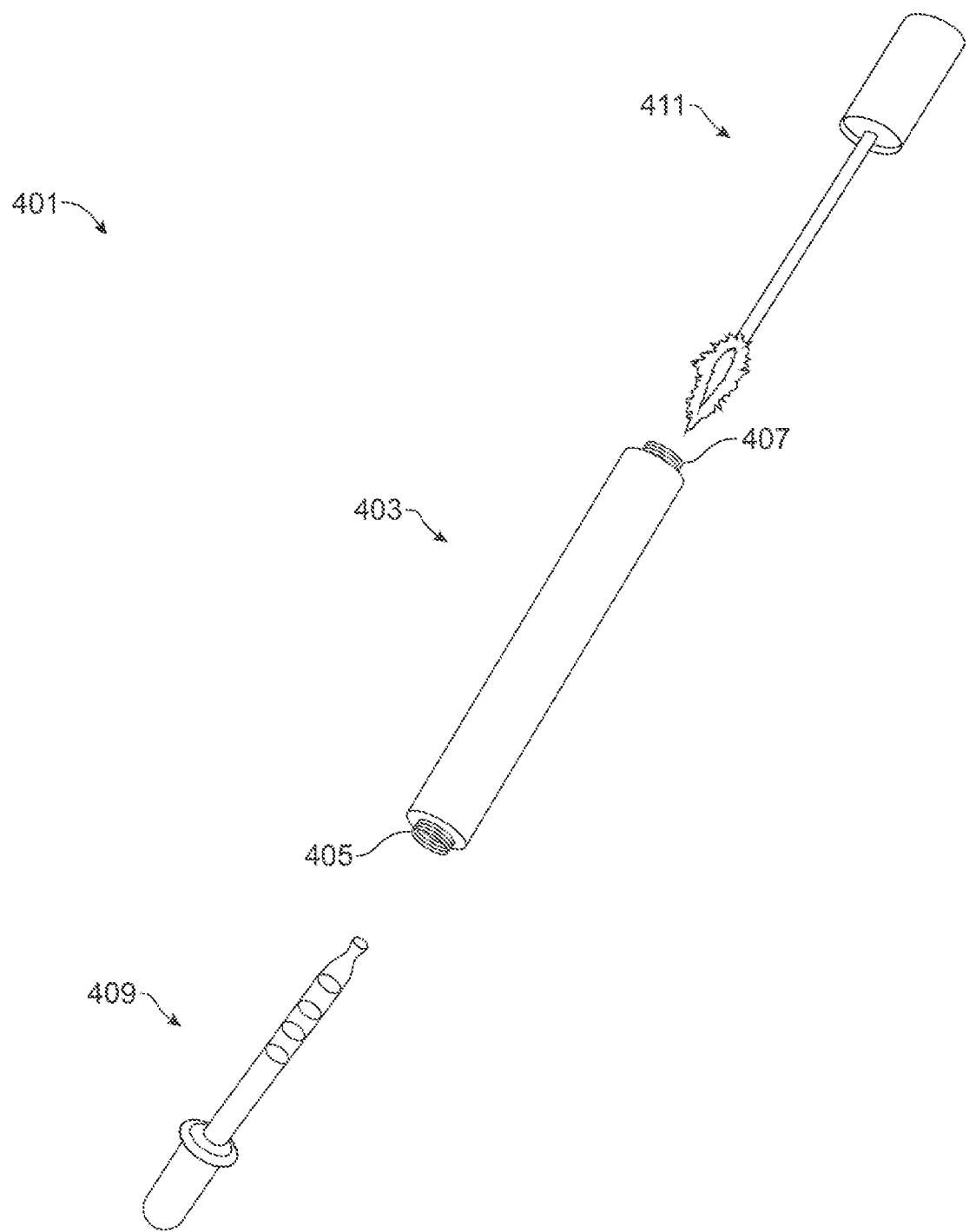
FIG. 11 is a perspective view of the third module in the embodiment of FIGS. 2-4.

The second module 207 is attached to a third module 271 (shown in greater detail in FIGS. 11-13) by way of a rotatable joint 273 (shown in greater detail in FIGS. 5-7). The rotatable joint 273 may be a ball joint, a swivel joint or another type of joint that allows movement of the second module 207 relative to the third module 271, and preferably in at least one direction perpendicular to the longitudinal axis of the joint. The third module in this particular embodiment is equipped with a filter 275. The filter 275 is preferably a wire mesh, but may comprise other suitable filtering materials as are known to the art. The third module 271 is further equipped with male threading 277 on one end thereof.

Figure 4:
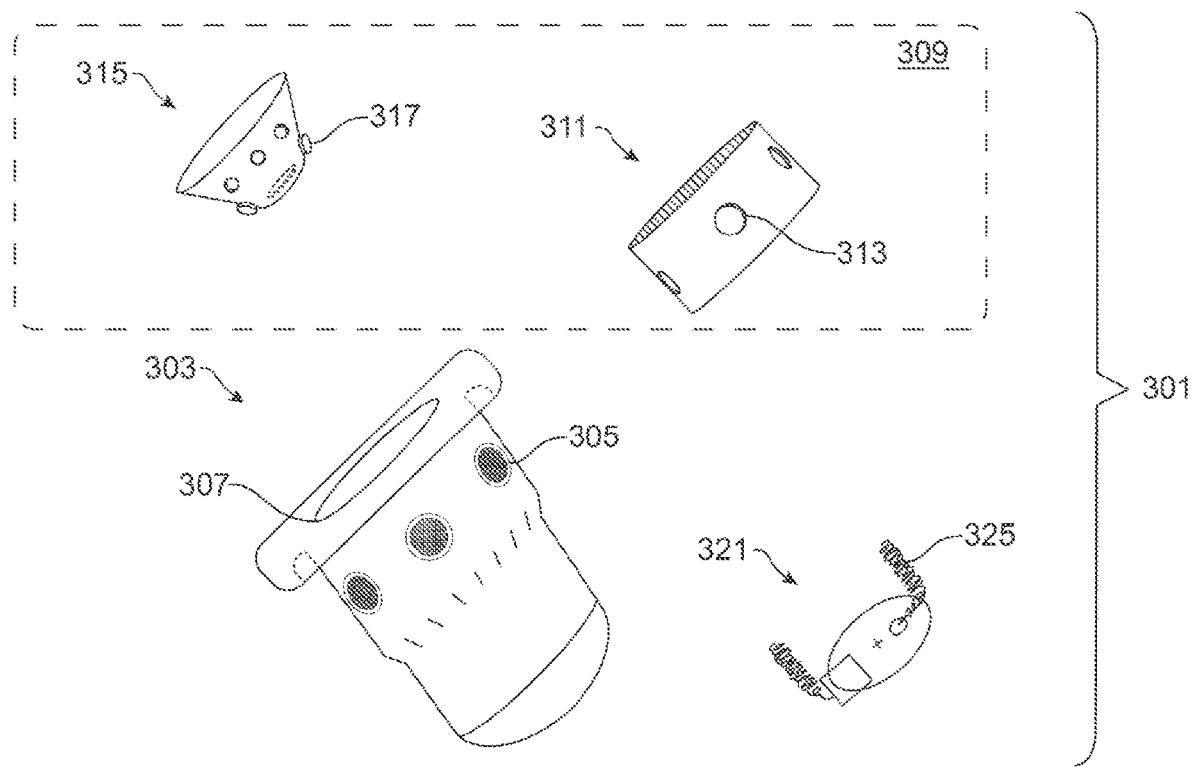

FIG. 4 depicts a fourth module 301 which releasably engages the third module 271 and, in particular, the male threading 277 thereof. The fourth module 301 has an exterior body 303 which is equipped with a plurality of apertures 305. The exterior body 303 is equipped with a resilient opening 307 which releasably engages the third module 271 as described above. In some embodiments, the exterior body 303 is equipped with an elastomeric lip or O-ring which serves as the resilient opening. In other embodiments, the entire exterior body 303, or a portion thereof, is fashioned from a suitable elastomeric or resilient material.

The fourth module 301 further includes a thermally conductive container 309 which sits inside of the exterior body 303. The thermally conductive container 309 includes a conical portion 311 which is equipped with a plurality of apertures 313, and a frustoconical portion 315 which is also equipped with a plurality of apertures 317. The conical portion 311 and frustoconical portion 315 of the thermally conductive container 309 are depicted as discrete components, although in some embodiments, they may be present as portions of a singular component. The interior of the exterior body 303 is preferably complimentary in shape to the exterior of the thermally conductive container 309 so that the latter sits snugly within the exterior body 303.

The thermally conductive container 309 preferably comprises a thermally conductive metal such as, for example, aluminum, tin or copper, but may also comprise other thermally conductive materials such as, for example, polymeric materials, plastics, graphite or glass which have been compounded with suitable fillers to impart thermally conductive properties to them.

The fourth module 301 further includes a heating module 321. The heating module 321 in this particular embodiment comprises a battery 323 and a set of heating coils 325, and sits beneath the thermally conductive container 309 within the exterior body 303. The heating module 321 may be activated upon command by the user as, for example, by pressing a button disposed on the exterior of the device 201. Preferably, the heating module 321 is equipped with suitable circuitry which allow it to become deactivated when a predetermined threshold temperature is reached, or after a predetermined period of time.

Preferably, the fourth module 301 is constructed out of inexpensive materials, and is designed to be disposable. This allows the fourth module 301 to be easily and economically replaced after it has become dirty (for example, through accumulation of tar or other debris) with use, without having to replace the rest of the device 201.

In use, the first module 205 is disconnected from the second module 207. A suitable condensate (preferably a wax dab) is then placed in the thermally conductive container 309 of the device 201. The thermally conductive container 309 is then heated by the heating module 321, causing it to melt and vaporize or combust. The user then places their mouth over the second module 205 (or over a suitable mouthpiece in fluidic communication with the second module) and inhales. A fluidic flow path exists between the second module 207, the rotatable joint 273, the third module 271, and the apertures 305 of the fourth module 301. Consequently, air is withdrawn from the ambient environment, mixes with the volatilized components of the heated condensate, and forms a THC-laden smoke that is ultimately inhaled by the user.

FIG. 6 depicts a third particular, non-limiting embodiment of a device for the self-administration of cannabinoids in accordance with the teachings herein. The device 401 depicted therein includes a central container 403 having first 405 and second 407 openings on first and second opposing ends thereof. A first applicator 409 is releasably engaged in the first opening 405, and a second applicator 411 is releasably engaged in the second opening 407. In the particular embodiment depicted, the first applicator 409 is an eyedropper which may be used, for example, for the application of drops of liquid (such as, for example, THC disposed in a suitable liquid medium) to a user or to a suitable substrate (such as, for example, an edible material). The second applicator 411 is a brush, somewhat similar to an eyeliner, which may be used, for example, to apply a liquid (such as, for example, THC disposed in a suitable liquid medium) to a suitable substrate (such as, for example, the lips of a user). In some embodiments, either or both of the first and second openings may be provided with suitable threading that rotatingly engages complimentary threading provided on the first 409 and second 411 applicators to secure the same to the central container 403.

Various modifications are possible to the devices and methodologies disclosed herein without departing from the scope of the present disclosure. For example, the devices disclosed herein may be equipped with pressure-activated or flow-activated LED lighting so that the device is illuminated, or undergoes a color change, when it is drawn upon (as, for example, by inhaling smoke or vapor through the device). In some embodiments, the intensity of the illumination may vary with, or be proportional to, the pressure change or flow rate. In other embodiments, the color of the illumination may vary with the pressure change or flow rate.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims.

What is claimed is:

1. A device for the self-administration of cannabinoids, comprising:
   a first module which is equipped with a first set of threads and which has first and second opposing ends, said first module including
   (a) a first element equipped with first and second threading,
   (b) a receptacle equipped with at least one surface feature which slidingly engages said first set of threads, and
   (c) a solid medium which is seated in said receptacle and which contains at least one cannabinoid;
   a second module which is connected to the second end of said first module by way of a rotatable ball joint;
   a filter;
   a third module having an exterior body with a first plurality of apertures therein and equipped with
   (a) a resilient opening which releasably engages said second module, and
   (b) a thermally conductive container which sits in said exterior body; and
   a fluidic flow path which extends from said first plurality of apertures through said third module, said rotatable joint, said filter, said second module and said first and second opposing ends of said first module;
   wherein said thermally conductive container includes a conical portion and a frustoconical portion.

2. The device of claim 1, wherein said third module includes a heating module, and wherein said heating module includes a battery in electrical communication with a set of metal coils.

3. The device of claim 1, wherein said conical portion has a second plurality of apertures therein.

4. The device of claim 1, wherein said frustoconical portion has a third plurality of apertures therein.

5. The device of claim 1, wherein said filter is disposed within said second module.

6. The device of claim 1, wherein said second module is equipped with a second set of threads, and wherein said resilient opening of said third module extends over said second set of threads.

7. The device of claim 1, wherein said first module is conical in shape, and wherein said first set of threads are disposed on an interior surface of said first module.

8. A device for the self-administration of cannabinoids, comprising:
   a first module which is equipped with a first set of threads and which has first and second opposing ends, said first module including
   (a) a first element equipped with first and second threading,
   (b) a receptacle equipped with at least one surface feature which slidingly engages said first set of threads, and
   (c) a solid medium which is seated in said receptacle and which contains at least one cannabinoid;
   a second module which is connected to the second end of said first module by way of a rotatable ball joint;
   a filter;
   a third module having an exterior body with a first plurality of apertures therein and equipped with
   (a) a resilient opening which releasably engages said second module, and
   (b) a thermally conductive container which sits in said exterior body; and
   a fluidic flow path which extends from said first plurality of apertures through said third module, said rotatable joint, said filter, said second module and said first and second opposing ends of said first module;
   wherein said filter is disposed within said second module.

9. The device of claim 8, wherein said third module includes a heating module, and wherein said heating module includes a battery in electrical communication with a set of metal coils.

10. The device of claim 8, wherein said filter is a metal mesh filter.

11. The device of claim 8, wherein said second module is equipped with a second set of threads, and wherein said resilient opening of said third module extends over said second set of threads.

12. The device of claim 8, wherein said first module is conical in shape, and wherein said first set of threads are disposed on an interior surface of said first module.

13. A device for the self-administration of cannabinoids, comprising:
- a first module which is equipped with a first set of threads and which has first and second opposing ends, said first module including
  - (a) a first element equipped with first and second threading,
  - (b) a receptacle equipped with at least one surface feature which slidingly engages said first set of threads, and
  - (c) a solid medium which is seated in said receptacle and which contains at least one cannabinoid;
- a second module which is connected to the second end of said first module by way of a rotatable ball joint;
- a filter;
- a third module having an exterior body with a first plurality of apertures therein and equipped with
  - (a) a resilient opening which releasably engages said second module, and
  - (b) a thermally conductive container which sits in said exterior body; and
- a fluidic flow path which extends from said first plurality of apertures through said third module, said rotatable joint, said filter, said second module and said first and second opposing ends of said first module;
- wherein said second module is equipped with a second set of threads, and wherein said resilient opening of said third module extends over said second set of threads.

14. The device of claim 13, wherein said third module includes a heating module, and wherein said heating module includes a battery in electrical communication with a set of metal coils.

15. The device of claim 13, wherein said filter is a metal mesh filter.

16. The device of claim 13, wherein said frustoconical portion has a third plurality of apertures therein.

17. The device of claim 13, wherein said first module is conical in shape, and wherein said first set of threads are disposed on an interior surface of said first module.

18. A device for the self-administration of cannabinoids, comprising:
- a first module which is equipped with a first set of threads and which has first and second opposing ends, said first module including
  - (a) a first element equipped with first and second threading,
  - (b) a receptacle equipped with at least one surface feature which slidingly engages said first set of threads, and
  - (c) a solid medium which is seated in said receptacle and which contains at least one cannabinoid;
- a second module which is connected to the second end of said first module by way of a rotatable ball joint;
- a filter;
- a third module having an exterior body with a first plurality of apertures therein and equipped with
  - (a) a resilient opening which releasably engages said second module, and
  - (b) a thermally conductive container which sits in said exterior body; and
- a fluidic flow path which extends from said first plurality of apertures through said third module, said rotatable joint, said filter, said second module and said first and second opposing ends of said first module;
- wherein said first module is conical in shape, and wherein said first set of threads are disposed on an interior surface of said first module.

19. The device of claim 18, wherein said third module includes a heating module, and wherein said heating module includes a battery in electrical communication with a set of metal coils.

20. The device of claim 18, wherein said filter is a metal mesh filter.

* * * * *